United States Patent
Wood

(10) Patent No.: US 7,115,893 B1
(45) Date of Patent: Oct. 3, 2006

(54) CHEMICAL AGENT SENSOR HAVING A STATIONARY LINEAR FRINGE INTERFEROMETER

(75) Inventor: Roland A. Wood, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 231 days.

(21) Appl. No.: 10/819,496

(22) Filed: Apr. 7, 2004

Related U.S. Application Data

(63) Continuation-in-part of application No. 10/324,314, filed on Dec. 19, 2002, now Pat. No. 6,946,644.

(51) Int. Cl.
*G01N 15/06* (2006.01)

(52) U.S. Cl. .................... 250/573; 250/574; 250/222.2

(58) Field of Classification Search ................ 250/573, 250/226, 222.2, 574
See application file for complete search history.

(56) References Cited

U.S. PATENT DOCUMENTS

| | | | |
|---|---|---|---|
| 4,472,239 A | | 9/1984 | Johnson et al. |
| 4,496,839 A | * | 1/1985 | Bernstein et al. ........ 250/341.6 |
| 5,220,189 A | | 6/1993 | Higashi et al. |
| 5,241,179 A | * | 8/1993 | Carrieri .................... 250/341.6 |
| 5,539,518 A | | 7/1996 | Bennett |
| 5,774,215 A | | 6/1998 | Padgett et al. |
| 5,895,233 A | | 4/1999 | Higashi et al. |
| 6,157,404 A | | 12/2000 | Marshall et al. |
| 6,277,666 B1 | | 8/2001 | Hays et al. |

| | | |
|---|---|---|
| 2002/0024664 A1 | 2/2002 | Yokota et al. |

FOREIGN PATENT DOCUMENTS

| | | |
|---|---|---|
| EP | 0809298 | 11/1997 |
| EP | 0973019 | 1/2000 |
| EP | 1022551 | 7/2000 |

OTHER PUBLICATIONS

Flanigan, Dennis F., "Detection of organic vapors with active and passive sensors: a comparison," Applied Optics, vol. 25 No. 23, pp. 4253-4260, Dec. 1, 1986.

Flanigan, Dennis F., "Prediction of the limits of detection of hazardous vapors by passive infrared with the use of MODTRAN," Applied Optics, vol. 35, No. 30, pp. 6090-6098, Oct. 20, 1996.

Foote, et al., "High performance micromachined thermopile linear arrays," SPIE vol. 3379, Part of the SPIE Conference on Infrared Detectors and Focal Plane Arrays V., Orlando, Florida, pp. 192-197, Apr. 1998.

Graham et al., "The Performance and Scientific Rationale for an Infrared Imaging Fourier Transform Spectrograph on a Large Space Telescope," Publications of the Astronomical Society of the Pacific, vol. 110, pp. 1205-1215, Oct. 1998.

Harig et al., "Scanning Infrared Remote Sensing System for Identification, Visualization, and Quantification of Airborne Pollutants," Society of Photo-Optical Instrumentation Engineers, 11 Pages, 2001.

(Continued)

*Primary Examiner*—Que T. Le
(74) *Attorney, Agent, or Firm*—Kris T. Fredrick

(57) ABSTRACT

A sensor having an input to an interferometer. The input may receive emissions from a detected fluid. The output of the interferometer may be focused on an array of light detectors. Electrical signals from the detectors may go to a processor. The output of the processor may include a spectrum of the detected fluid. Also, the identity of the fluid may be determined.

29 Claims, 21 Drawing Sheets

OTHER PUBLICATIONS http://www.spie.org/conferences/programs/01/pb/confs/4574.html, "Instrumentation for Air Pollution and Global Atmospheric Monitoring," 5 Pages, Printed Apr. 25, 2004.

Kruse, Application of Uncooled Monolithic Thermoelectric Linear Arrays to Imaging Radiometers, Uncooled Infrared Imaging Arrays and Systems, Semiconductors and Semimetals, vol. 47, Chapter 10, pp. 297-318, Copyright 1997 by Academic Press.

Steers et al., "Gasoline analysis and brand identification using a static Fourier-transform ultraviolet spectrometer," J. Opt. A: Pure Appl. Opt. 1, pp. 680-684, 1999.

Teranishi, "Thermoelectric Uncooled Infrared Focal Plane Arrays," Uncooled Infrared Imaging Arrays and Systems, Semiconductors and Semimetals, vol. 47, Chapter 6, pp. 203-218, Copyright 1997 by Academic Press.

* cited by examiner

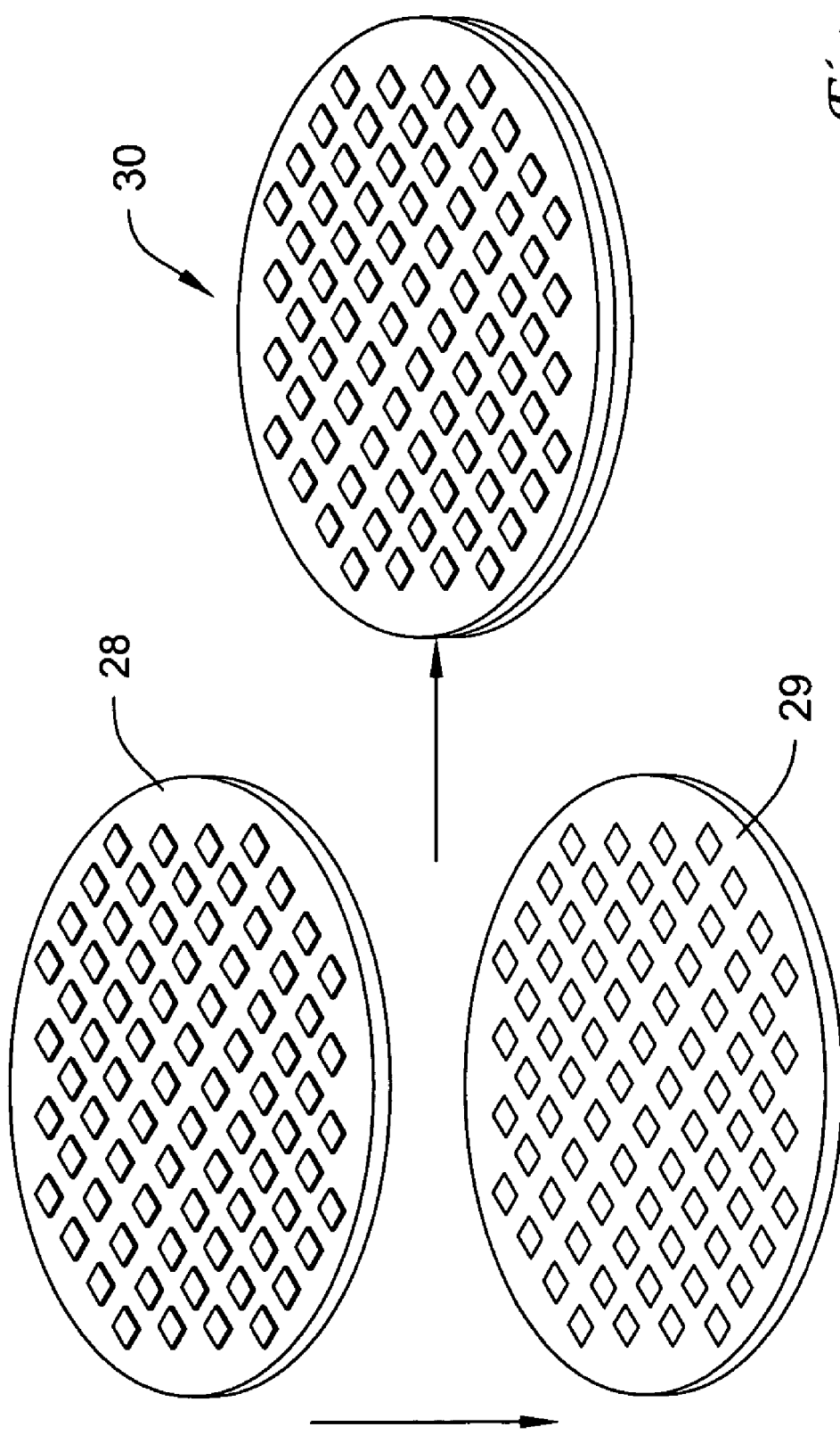

Weight Calculation for single-band Chemical Agent sensor

| | Length (mm) | Width (mm) | Thickness (mm) | Volume (cc) | Density (gm/cc) | Wt (gm) |
|---|---|---|---|---|---|---|
| 30x30 TE mosaic array | 5 | 5 | 0.5 | 0.013 | 2.34 | 0.030 |
| IVP top cap | 4 | 5 | 0.4 | 0.008 | 2.34 | 0.019 |
| Preamps | 5 | 5 | 0.4 | 0.01 | 2.34 | 0.024 |
| Micro Processor | 5 | 10 | 0.4 | 0.02 | 2.34 | 0.048 |
| Misc. chips | 25 | 25 | 0.4 | 0.25 | 2.34 | 0.59 |
| Resistors and capacitors | | | | 0.5 (est.) | 2.5(est.) | 1.25 |
| Gold traces | 25 | 25 | 0.05 | 0.031 | 19.31 | 0.60 |
| Ceramic motherboard | 10 | 10 | 0.5 | 0.05 | 4.0 | 0.20 |
| PbSn solder | 25 | 15 | 0.2 | 0.075 | 11.4 | 0.855 |
| Optical baffles | 20 | 0.1 | 0.1 | 0.0002 | 4.5 | 0.001 |
| Ge window | 10 | 10 | 0.5 | 0.05 | 5.33 | 0.27 |
| Total Weight (gm) | | | | | | 3.89 |

Fig.13

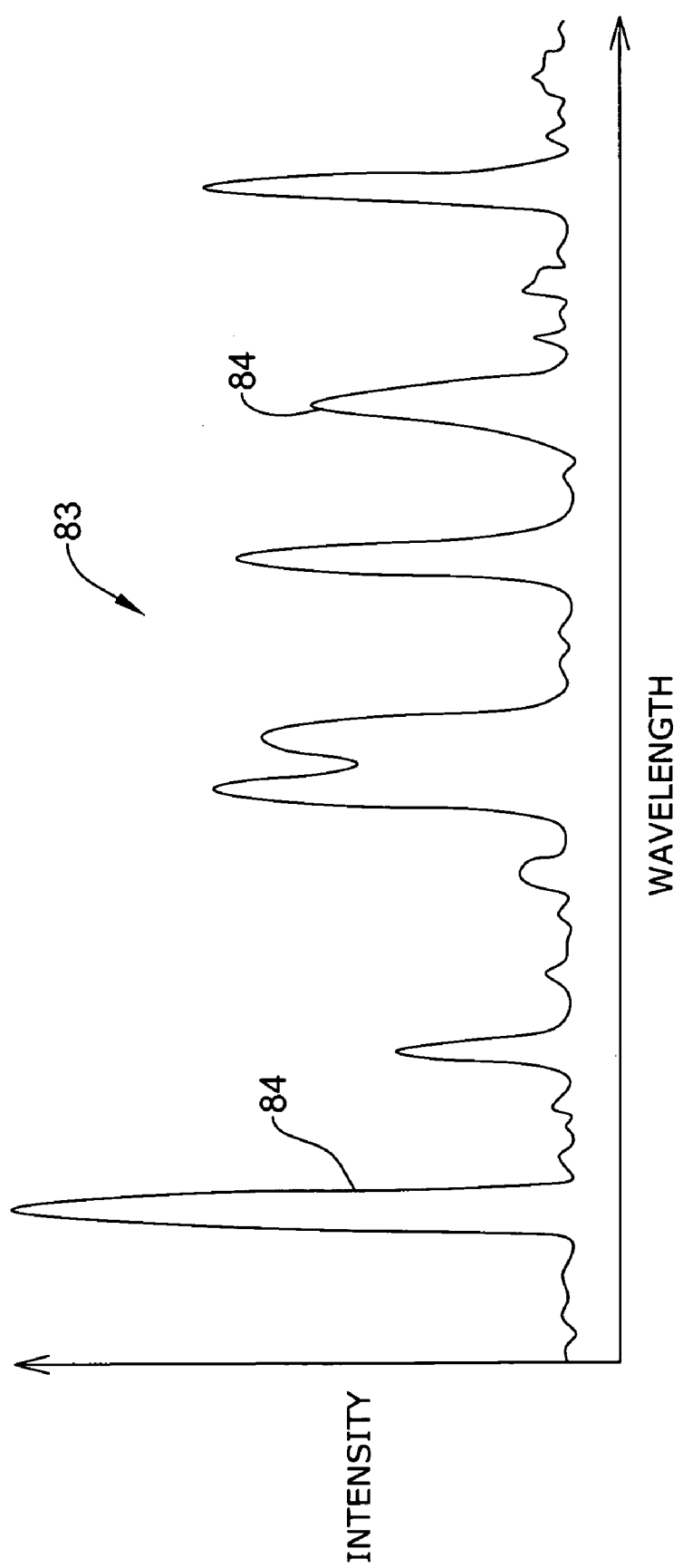

CHEMICAL AGENT SENSOR HAVING A STATIONARY LINEAR FRINGE INTERFEROMETER

BACKGROUND

This present application is a continuation-in-part of U.S. patent application Ser. No. 10/324,314, filed Dec. 19, 2002, now U.S. Pat. No. 6,946,644, by R. A. Wood, and entitled "MULTI-BAND SENSOR".

The invention may pertain to sensors and in particular to sensors for detecting the presence of fluids and other substances. More particularly, the invention may pertain to sensors that have detector sensitivities of several bandwidths. "Fluid" is a generic term that includes liquids and gases as species. For instance, air, water, oil, gas and agents may be fluids.

The related art might detect at several wavelengths; however, the results of detection may not be sufficiently accurate because of sensor structure or other impediments resulting in different fields of view for detection at different wavelengths.

SUMMARY

The invention may be a multi-band sensor for detecting various fluids having emissions with various wavelengths and intensities.

BRIEF DESCRIPTION OF THE DRAWING

FIGS. 4a and 4b reveal the sensor in conjunction with a vacuum package;

FIG. 13 is a table of dimensions for a sensor;

FIG. 16 is a graph of a spectrum of a detected gas or gases.

DESCRIPTION

The device may be a multi-band sensor for chemical agents or other substances in the atmosphere, suitable for flight on micro air vehicles (MAVs), dispersal from aircraft, or other low-cost light-weight applications. The sensor may sense the infrared (IR) emission at several selected narrow wavebands in the 3–5 or 8–12 μm IR spectral region at which gases (exhaust fumes, chemical agents, etc.) show characteristic "fingerprint" infrared absorption and emission lines. The sensor may use uncooled silicon micromachined IR detectors in a silicon vacuum package. The sensors and detectors may be any kind of technology. IR detectors are an illustrative example here. The estimated size, weight and power of a complete sensor (less downlink transmitter and battery) are 1 cc, 4 grams, 0.5 mW.

The sensor may be a multi-band IR sensor with a field of view directed upwards (dispersed or ground-based sensor) or downwards (MAV sensor) depending on the mission purpose. For exhaust gas detection, at least one IR band may be centered on the absorption line of a component of exhaust gas ($CO_2$, $H_2O$, CO, $NO_x$, depending on the engine and fuel type), and at least one IR band may be centered at a wavelength where these gases are transparent. The presence of exhaust gases may be indicated by an imbalance in the measured radiance at the two or more wavelengths. The imbalance may be produced by the different emissivity and temperature of exhaust gas components. For a downward looking MAV sensor, this imbalance may show a daily reversal of polarity, with crossover (minimum sensitivity) in the morning and evening.

Figure 1A:
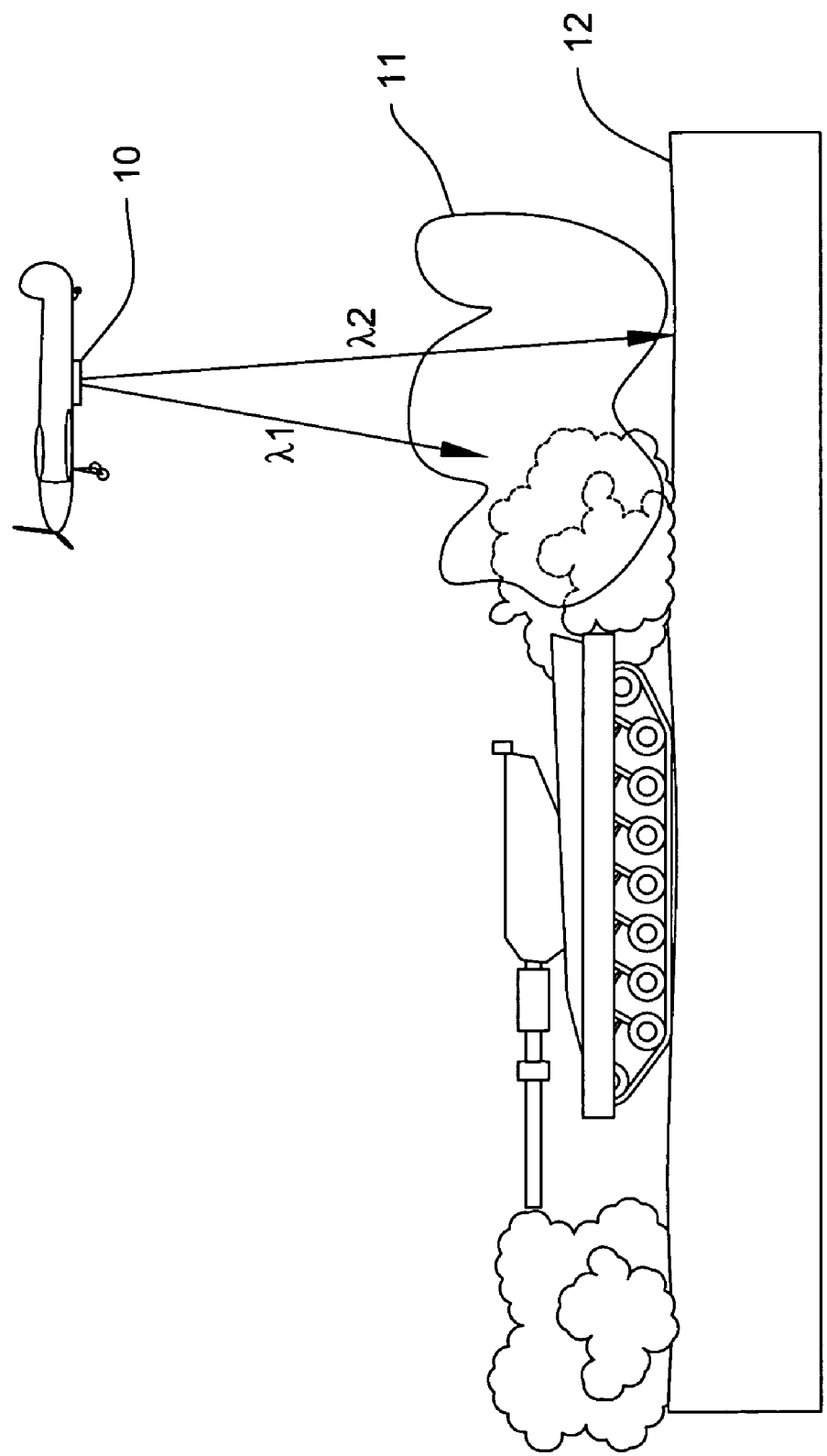
FIGS. 1a, 1b and 1c show upward and downward fields of view for a sensor.
Figure 1B:
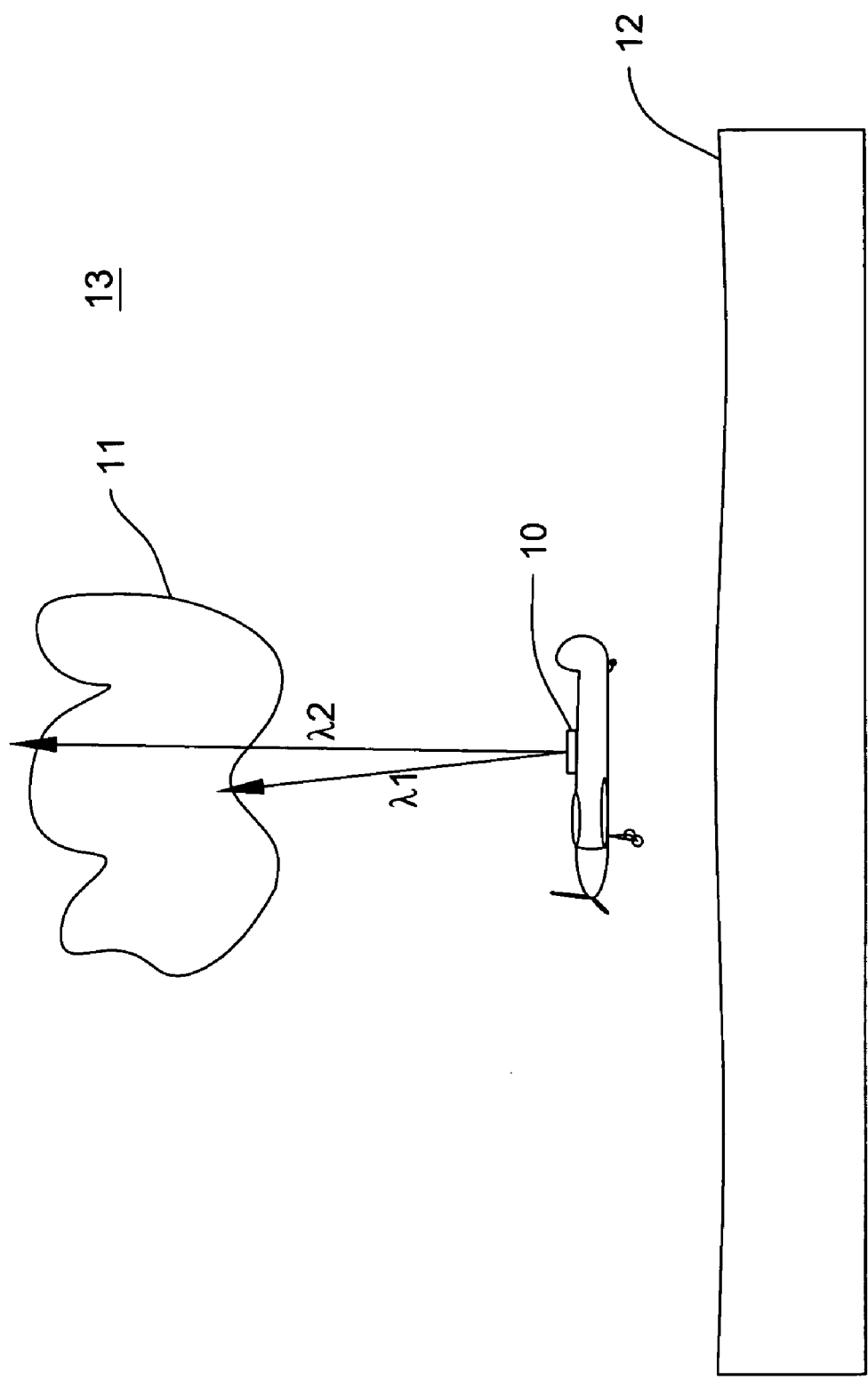
Figure 1C:
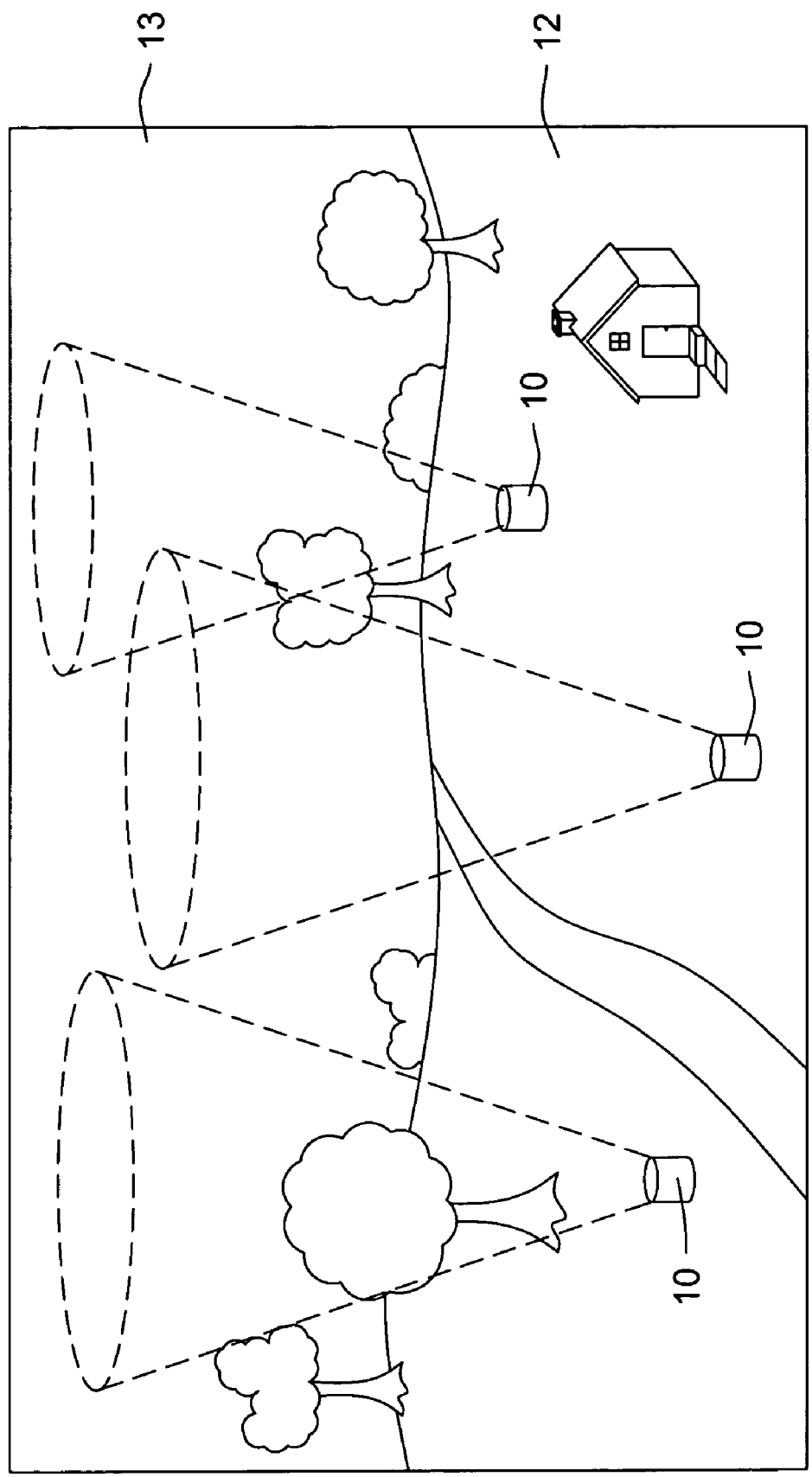
Figure 2:
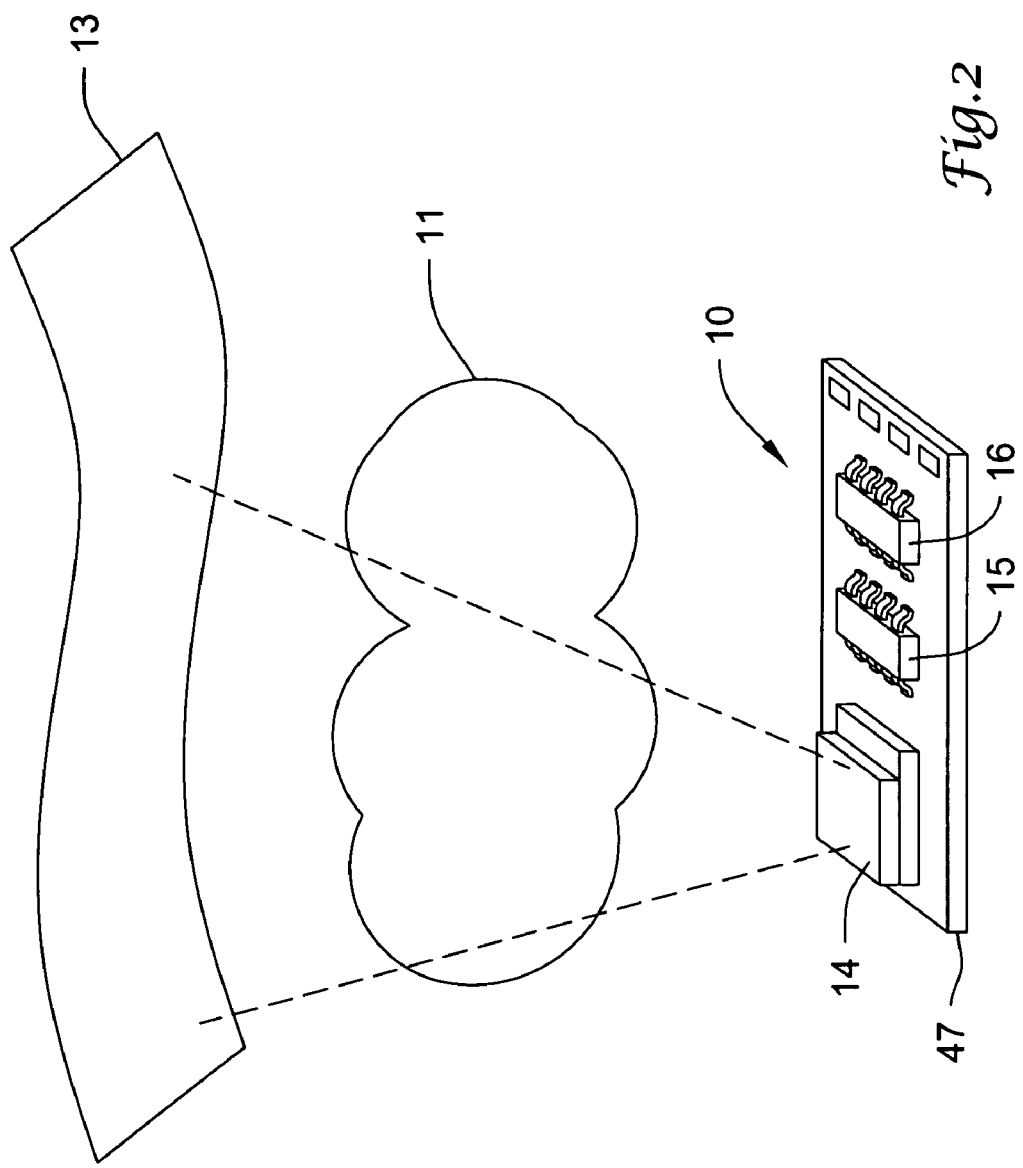
FIG. 2 shows the sensor relative to a gas cloud and the sky.
Figure 3:
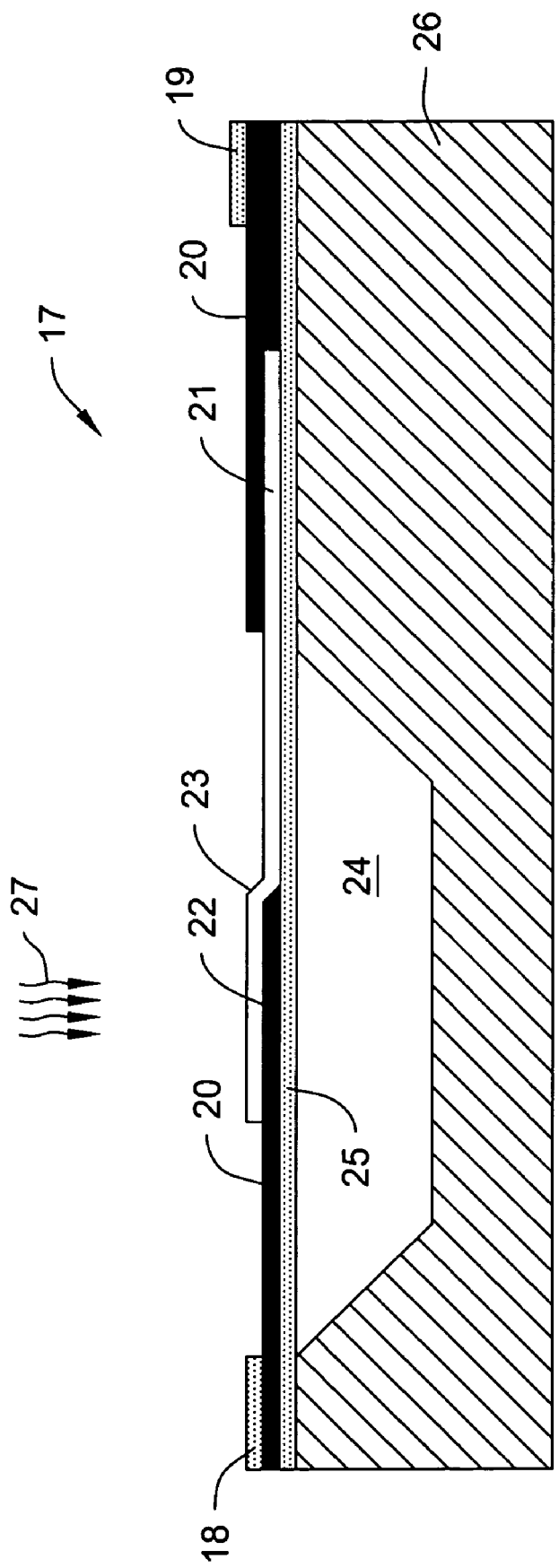
FIG. 3 illustrates a thermoelectric detector.

The magnitude of the imbalance is difficult to predict analytically for a MAV downward looking sensor, since it may be strongly dependent on time of day, wind dispersal, etc., but may be easily measurable, since engines produce large volumes of exhaust gases (a 1000 cu inch engine produces about 100 liters per second at 1000 rpm idle).

An estimate of sensitivity may be more tractable for an upward looking sensor. It may be shown with calculations that hazardous chemical agents could be detected by an upward looking IR sensor. Such sensor may operate by sensing the radiance change caused by IR emission from the agent dispersed at altitudes where the air temperature is different from the apparent sky temperature. Using GB (Sarin), a particular chemical nerve agent, as an example, and assuming a local air temperature 1 degree C. different from the apparent sky temperature, C=10 mg/m3 of GB dispersed in a cloud L=10 m thick would produce an apparent temperature change of about 100 mK in a 20 cm-1 IR band centered at 1020 cm-1. The apparent sky temperature change induced in a nearby IR band where GB is transparent (1250 cm-1, 8.0 um for example) is negligible in comparison. The IR signal from such a cloud of GB may therefore be detected (S/N≈5 for CL≈1100 mg/m2) with a very low false alarm rate (about 2 e–6) with an IR sensor with a noise equivalent target temperature difference (NETD) of 20 mK in a 20 cm-1 radiation bandwidth 1020 cm-1. To cancel out variations in the sky temperature, the sensor would measure the fractional change in radiance with two IR sensors fitted with narrow-band IR transmission filters (e.g., for GB, 20 cm-1 bands at 9.8 and 8.0 um).

FIGS. 1a and 1b are illustrations of a downward-looking and an upward-looking sensor 10, respectively, with two IR detectors operating at narrow-band wavelengths λ1 and λ2, which sense the infrared radiance of a gas cloud 11 (λ1) and with a ground 12 or sky 13 background (λ2). FIG. 1c shows several upward-looking dispersed sensors 10 which may provide a protective surveillance of toxic agents for a specific area. FIG. 2 shows sensor 10 looking towards a warm gas cloud 11 being contrasted against a cold sky 13. Sensor 10 may have a multi-band IR array 14, amplifiers 15 and processor 16. More than two IR wavebands can be employed. An IR thermoelectric (TE) detector and an integrated vacuum package (IVP) may be applicable here. An illustrative example of such detector may be in U.S. Pat. No. 5,220,189, issued Jun. 15, 1993, with inventors Robert Higashi et al., and entitled "Micromechanical Thermoelectric Sensor Element", which is hereby incorporated by reference. An illustrative example of such package may be in U.S. Pat. No. 5,895,233, issued Apr. 20, 1999, with inventors Robert Higashi et al. and entitled Integrated Silicon Vacuum Micropackage for Infrared Devices", which is hereby incorporated by reference. The unit cell or detector of this sensor consists of a thin (8000 A) silicon nitride microbridge, typically 50 to 75 um square, over a pit micromachined in the underlying silicon substrate. Microelectomechanical systems (MEMS) techniques may be utilized in the making or fabrication of the invention. Information about MEMS may be provided in U.S. Pat. No. 6,277,666, issued Aug. 21, 2001, with inventors Kenneth Hays et al. and entitled "Precisely Defined Microelectromechanical Structures and Associated Fabrication Methods", which is hereby incorporated by reference. The sensors may operate by a thermal detection mechanism, i.e., incident IR radiation may heat the microbridge. Thin (1000 Å) thermoelectric metal films may form a thermocouple-pair and generate a direct voltage signal. Sensor 10 may be 'self zeroing' at any temperature, and hence may not require a temperature stabilizer or high-bit A/D. FIG. 3 shows a cross-section of a TE detector 17. It may have electrical contacts 18 and 19 situated on a metal 20, a cold TE junction 21 and a hot TE junction 22 of metals 20 and 23. Junction 22 is supported over an etched pit or well 24 by a silicon nitride bridge 25. All of this may be formed in and supported by a substrate 26. IR radiation 27 may impinge detector 17 which in response an electrical signal noting the impingement appears at contacts 18 and 19.

Figure 4A:
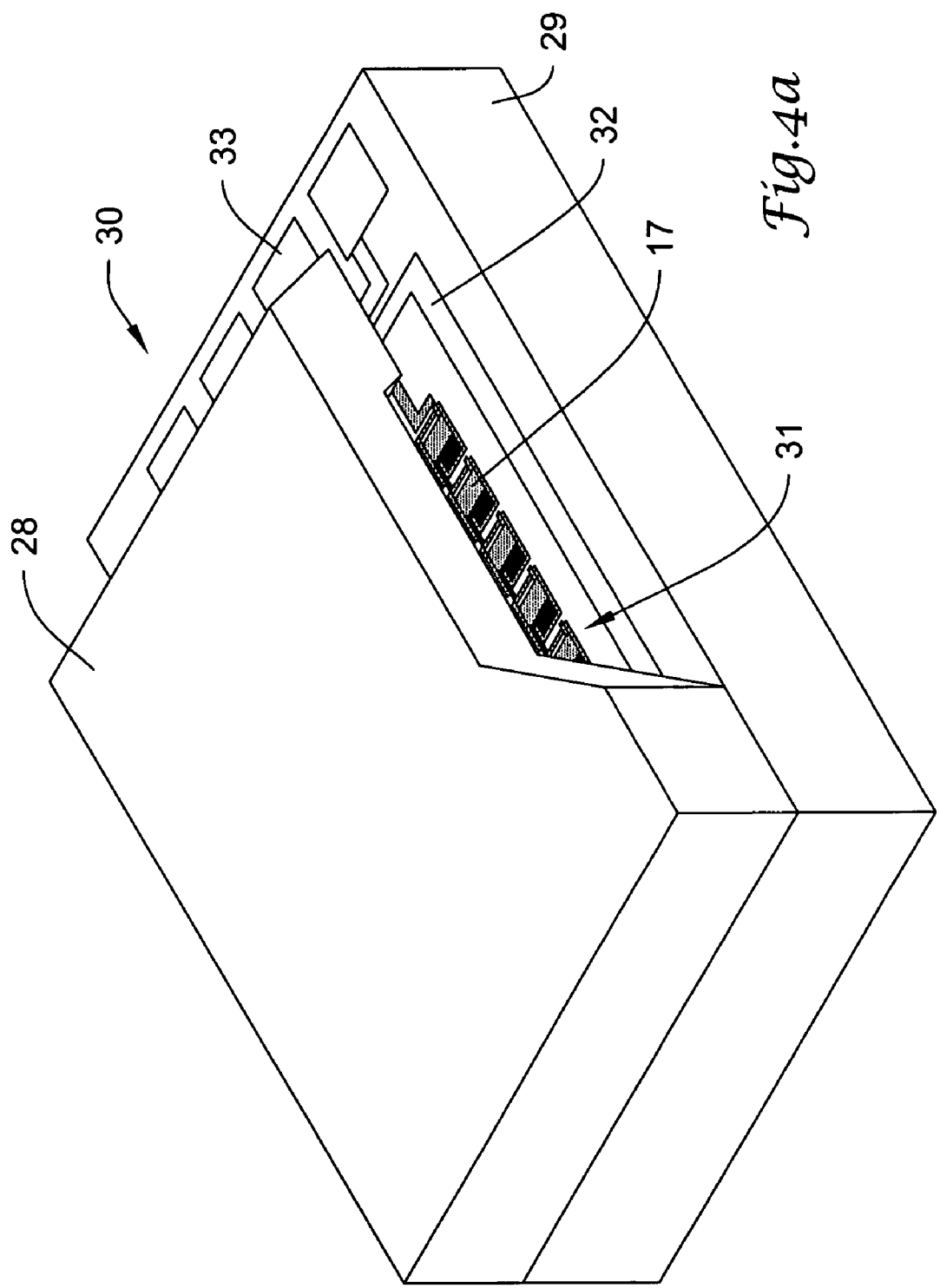

TE detectors 17 or sensors should operate in a vacuum to achieve full sensitivity (as any gas pressure more than 75 mTorr may dampen the thermal signals unacceptably). One may use a low-cost light-weight wafer-scale vacuum encapsulation using an IR-transparent silicon "topcap" 28 on a substrate 29 as shown in FIG. 4a. FIG. 4b illustrates the basic fabrication of wafer-to-wafer bonding of topcat wafer 28 to device wafer 29 to produce a low-cost vacuum package 30. Topcap 28 may be an anti-reflective coated silicon window. Item 30 is regarded as an integrated vacuum package (IVP). Between topcap 28 and substrate 29 is a cavity 31 that contains detectors 17. There is a seal ring 32 for wafer-to-wafer sealing of cavity 31 between topcap 28 and substrate 29. Gold pads 31 are for wire bonding the connections to detectors 17. Cavity 31 may be evacuated via a port through the back of substrate or wafer 29. This low-cost vacuum encapsulation adds negligible weight (i.e., about 0.02 grams) to detector array 14. A hermetically sealed 30×30 mosaic IVP TE sensor may have an overall die size of about 5 mm×5 mm.

For this non-imaging application, a 2D array is not required, but for adequate sensitivity it is necessary to use a mosaic of many individual TE detectors 17, electrically interconnected, to form a larger-area "mosaic" TE IR sensor 10, because the NETD improves as the square root of the mosaic area. Thus, a 30×30 mosaic is 30 times more sensitive than one unit cell 17, and can provide very good performance even with narrow radiation bandwidth. IVP sensors 14 have long vacuum lifetimes (over 10 years), operate up to 180° C., and can be easily handled like conventional silicon electronic chips. These IR sensors may be produced in volume production (i.e., thousands) at very little cost each.

Figure 5:
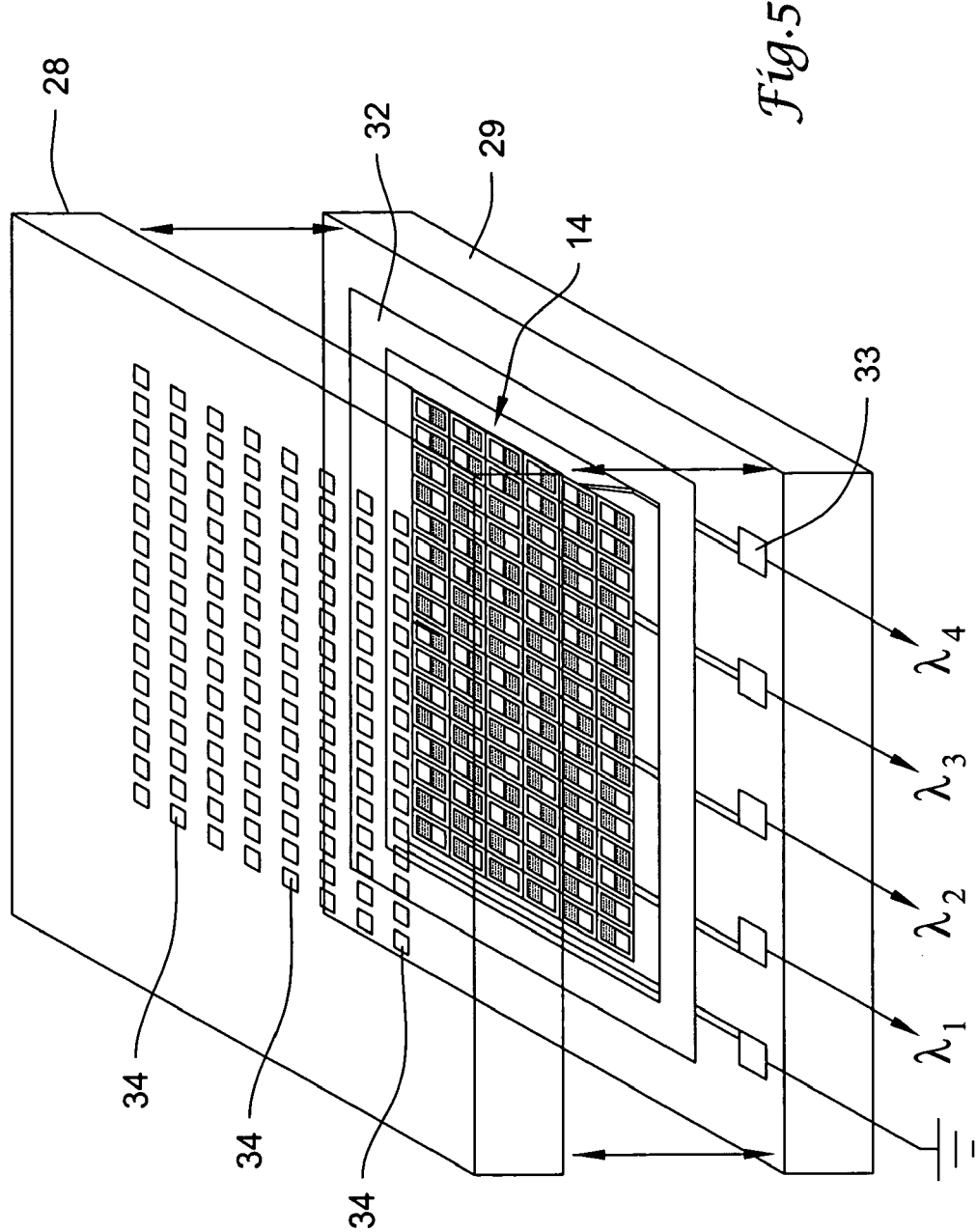
FIG. 5 is a layout of the detectors and filters of the sensor.
Figure 6:
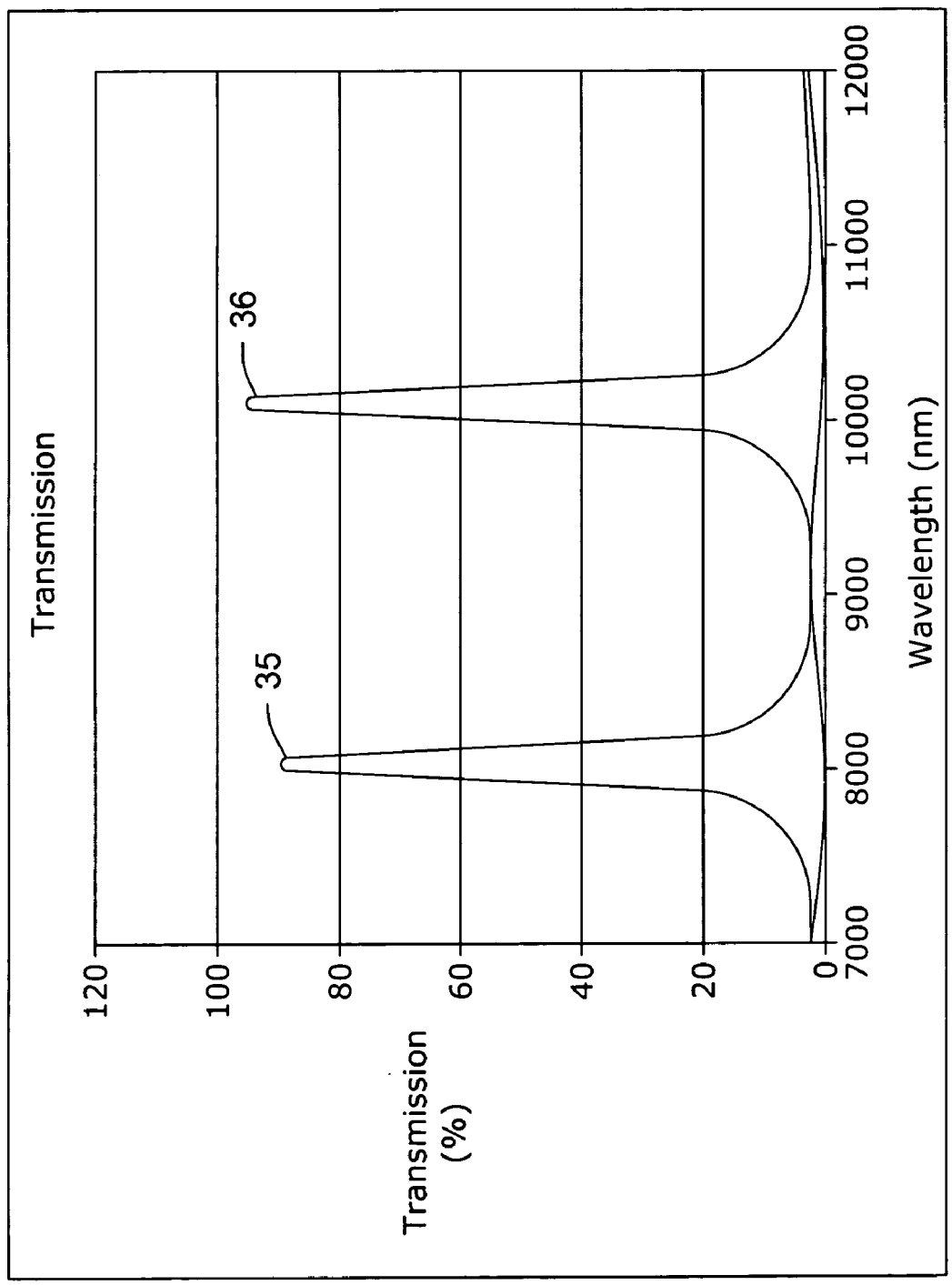
FIG. 6 is a graph showing transmission peaks of two thin-film interference filters.

FIG. 5 shows sensor 10 having multi-band capability utilizing a mosaic of IR bandpass filters. The multi-band capability of IR detectors 17 may be provided by fabricating narrow-band interference filters 34 directly on the inner surface of the IVP topcap 28 using a photolithographic process to generate alternating IR transmission bandpass filters with 75 um periodicity, matching the 75 um periodicity of the underlying TE detectors 17. A very simple dielectric stack may be employed to produce the selected IR bandpass filters. FIG. 6 reveals a calculated transmission of two thin-film interference filters (8 layers of Si and $SiO_2$) with transmission peaks 35 and 36 at 8 um and 10 um, respectively (20 cm-1 corresponds to about 200 nm wavelength width).

Figure 7:
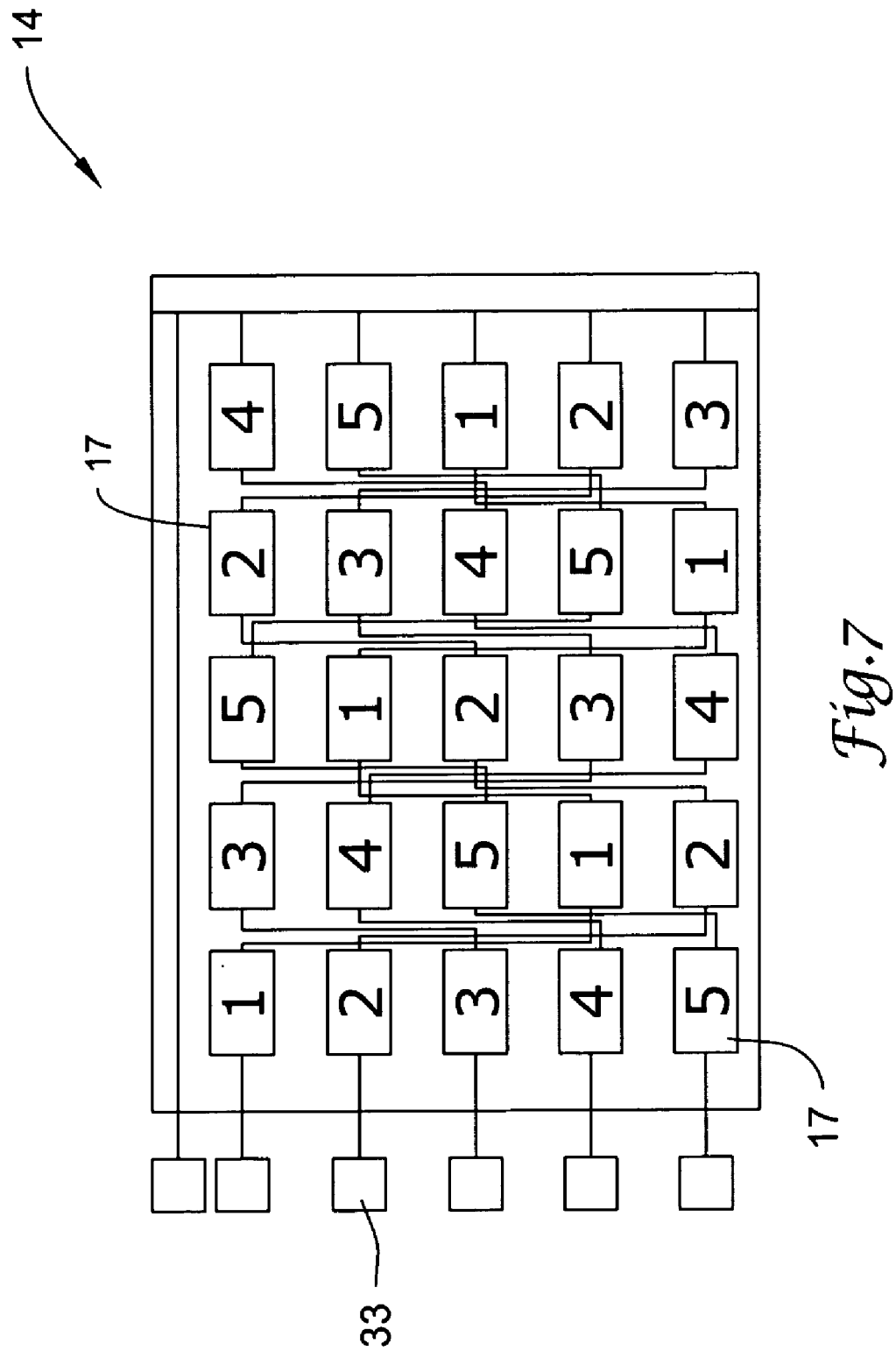
FIG. 7 is a layout of detectors and their connections into groups.

For a dual-band sensor, alternate TE detectors may be electrically interconnected in series and/or parallel, so that sensor 10 may automatically produce separate electrical signal voltages for each IR waveband, with approximately equivalent, about the same or essentially identical fields of view. A detector 17 near the edge of array 14 on substrate 29 may have a different field of view than a detector 17 in the center of array 14 because the side or edge of topcap 28 may obstruct part of the view from the outside to the detector 17 near the edge, whereas such obstruction would not be present for detector 17 in the center. There may be a number of detectors of the same wavelength in the array which make up a group of detectors 17. Detectors 17 of the same group and wavelength may be connected together with series or parallel electrical connections or a combination of such connections. The distribution of the detectors for the various wavelengths may be such that the group has a cumulative, composite, average or resultant field of view representative of the group's constituent detectors 17. The result is that the fields of view of the groups may be essentially the same or equivalent. FIG. 7 shows an example of five groups of detectors 17, one group for each wavelength or "color". Detectors 17 labeled "1" are of group 1, labeled "2" are of group 2, and so on. The colors (i.e., various wavelengths) can be distributed according to a regular pattern, which probably may be designed differently for different numbers of colors, but the general principle is the same. The various "colored" detectors 17 comprising the mosaic are distributed across the mosaic area, so that each individual "color" detector 17 has a substantially-equal number of near neighbors of each of the other "colors". All individual detectors of each separate color are electrically connected together (either in series, parallel or a combination thereof) to give a single output signal of that "color" and incorporating a field of view for the respective group. There may be a case in which the colors are distributed randomly, which achieves substantially the same equalization of the fields of view among the groups, even though a regular pattern is not used. Various "colored" detectors 17 comprising the mosaic may be distributed randomly across the mosaic area, so that each individual "color" detector 17 has, on the average, a substantially-equal number of near neighbors of each of the other "colors". All individual detectors 17 of each separate color may be electrically connected together (either in series or parallel, but usually in series) to give a single output signal of that "color". The random configuration may work better when the number of detectors in array 14 is large (i.e., greater than 50).

Figure 8:
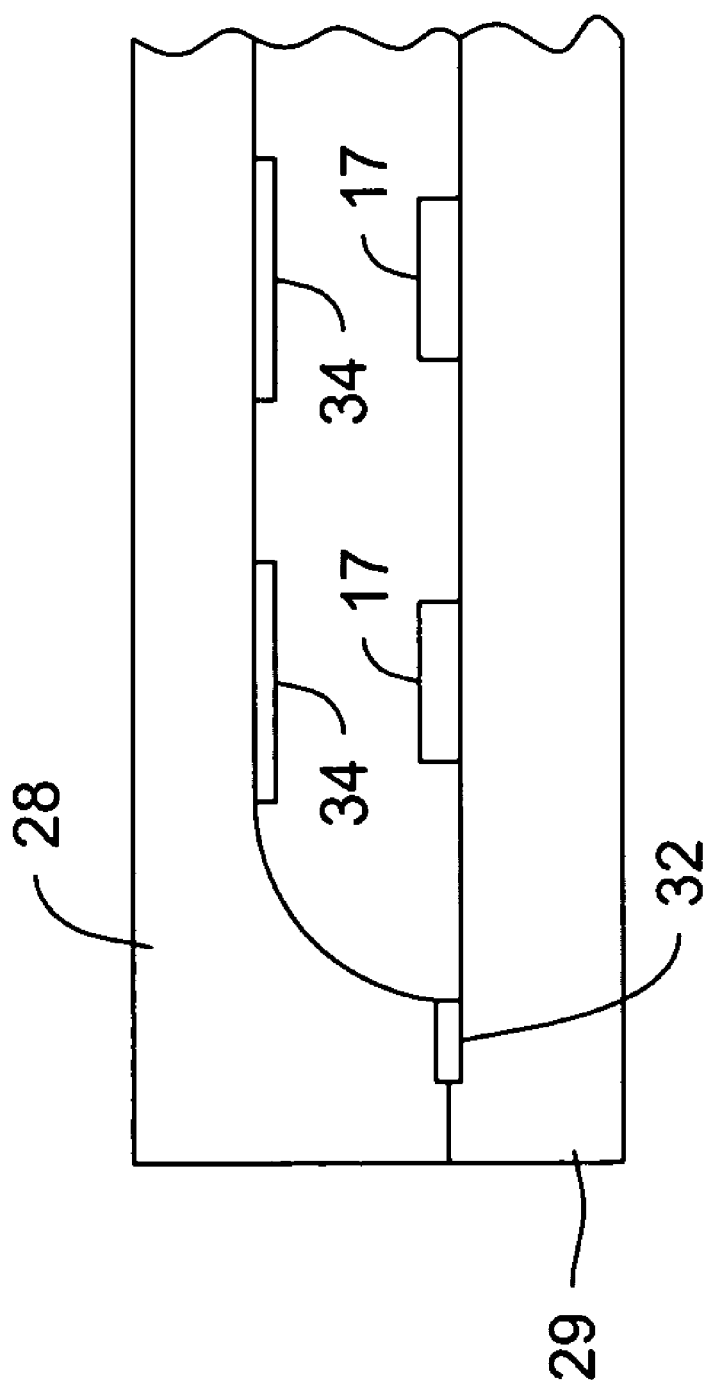
FIG. 8 is a side view of several detectors and their corresponding filters.

The wavelength or "color" of a detector 17 may be determined by the filter 34 situated between the sensing surface or junction of detector 17 and that which is observed. FIG. 5 reveals a perspective of filters 34 relative to detectors 17. Filters 34 designate the "colors" for detectors 17. The filters 34 are laid out according to groups as described above. FIG. 8 is a side view of the relationship of filter 34 to detector 17. Filters 34 may be put on the inside surface of topcap 28 with photolithographic processes.

The advantages of TE infrared thermal detectors 17 in the present sensor 10 include Low cost (because of the use of commercial silicon fabrication and vacuum package process), robustness (>12,000-g's, 180° C. tolerant, and European Space Agency space-qualified), suitability for long integration times (un-measurable 1/f sensor noise), high sensitivity (NETD <10 mK with 20 cm-1 IR bandwidth), broadband responsivity (<3 to >15 μm), and ease of operation (uncooled, no thermal stabilization or bias voltage required, direct dc signal voltage). Sensor 10 may utilize other kinds of detectors 17.

The NETD of a 2.5 mm square 30×30 mosaic IVP TE sensor 10 may be calculated to be <10 mK in the operating mode of the program with 10 seconds integration time, 20 cm-1 waveband near 10 um, 290 K target temperature, and F/1 optical aperture. The NESR may be computed to be 5.4 e–10 W/cm2.sr.cm-1. Two such IR detectors 17 may be placed side by side, viewing the sky via two IR thin-film multilayer filters 34 centered at (in the case of GB) 9.8 um and 8.0 um, to give a good signal/noise ratio (10:1 for CL=100 mg/m2) for GB under most atmospheric conditions.

Figure 9:
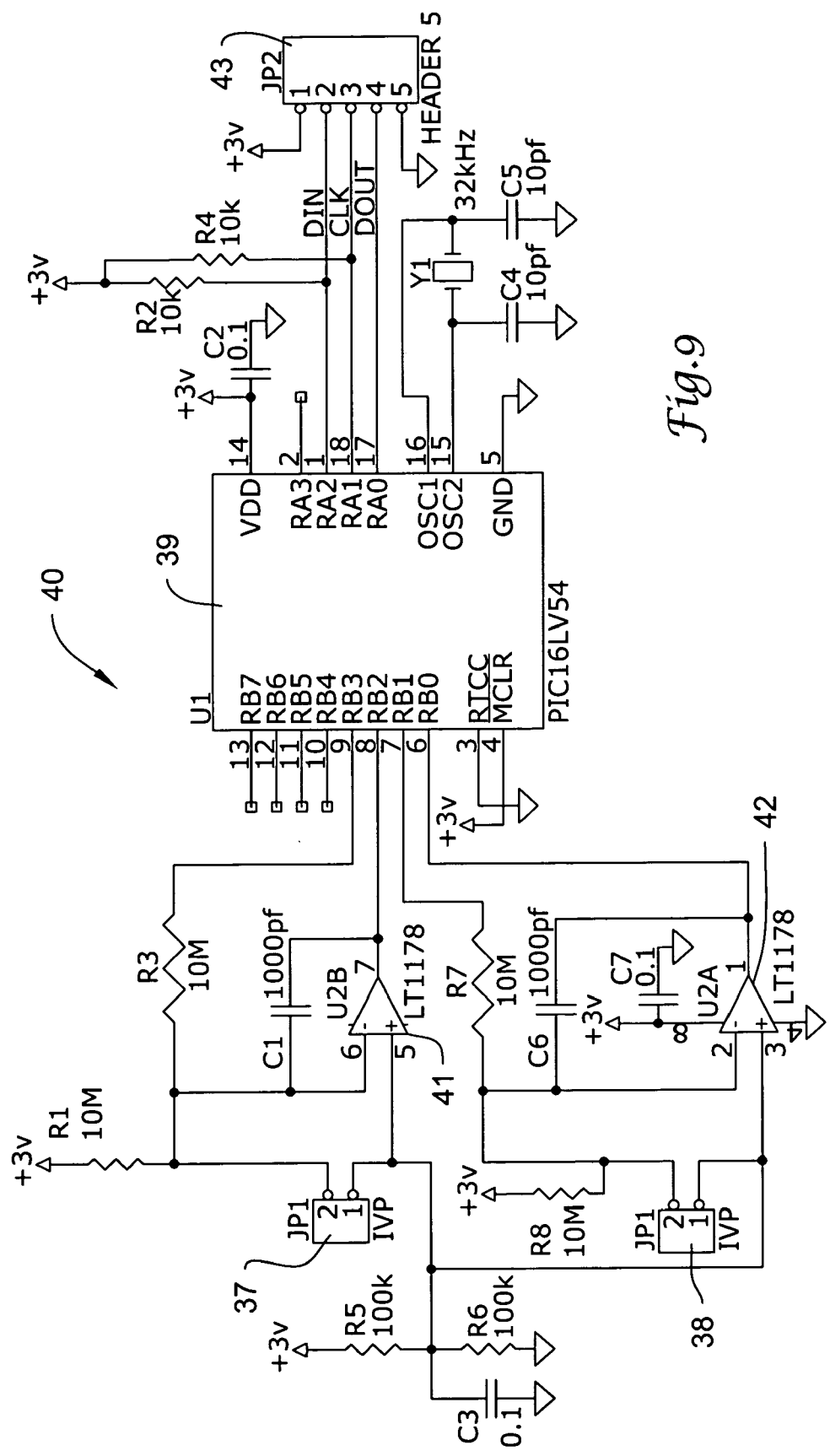
FIG. 9 is a schematic of some electronics for the sensor.
Figure 10A:
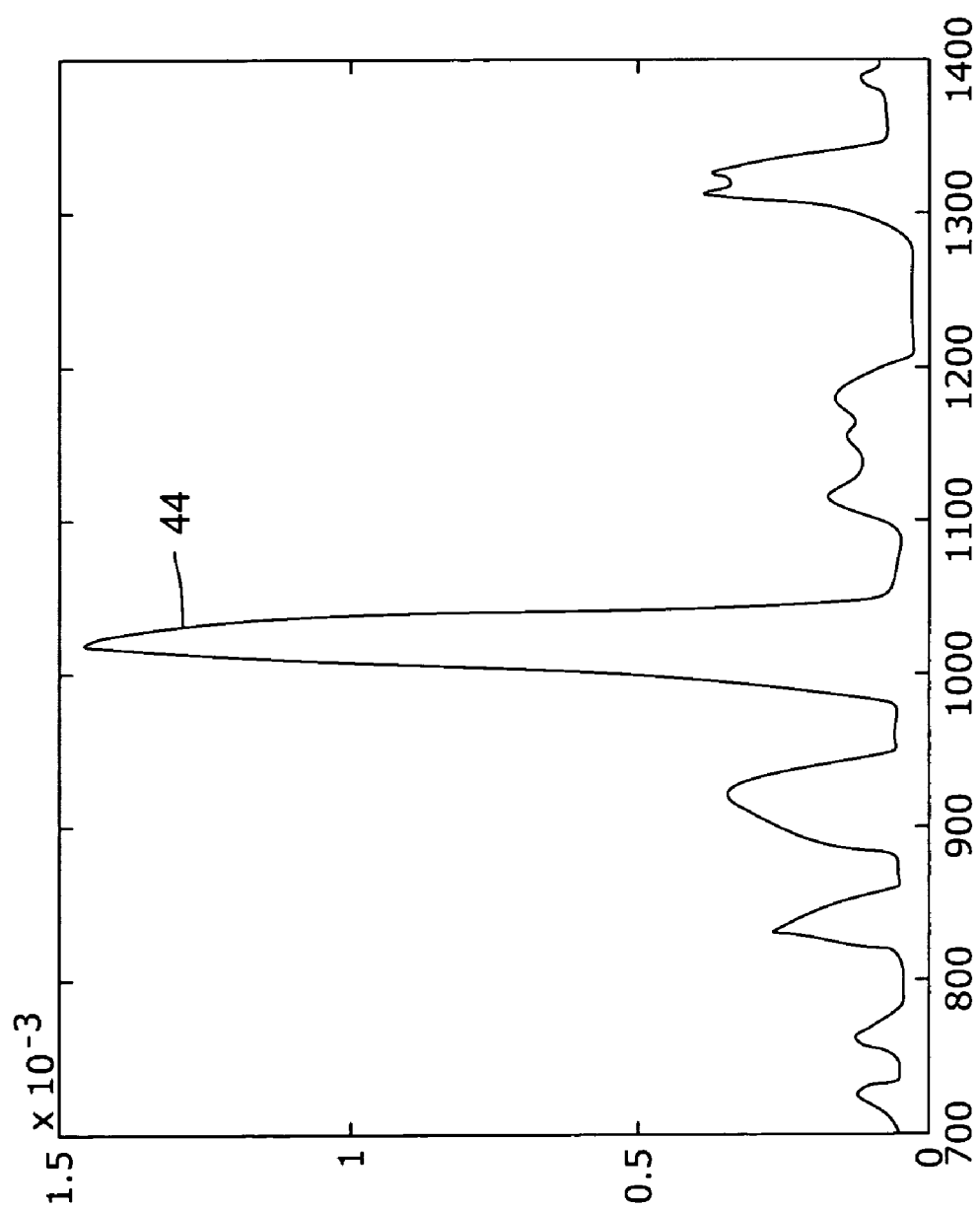
FIGS. 10a, 10b and 10c show absorptivity coefficients of an agent and two interferents.
Figure 10B:
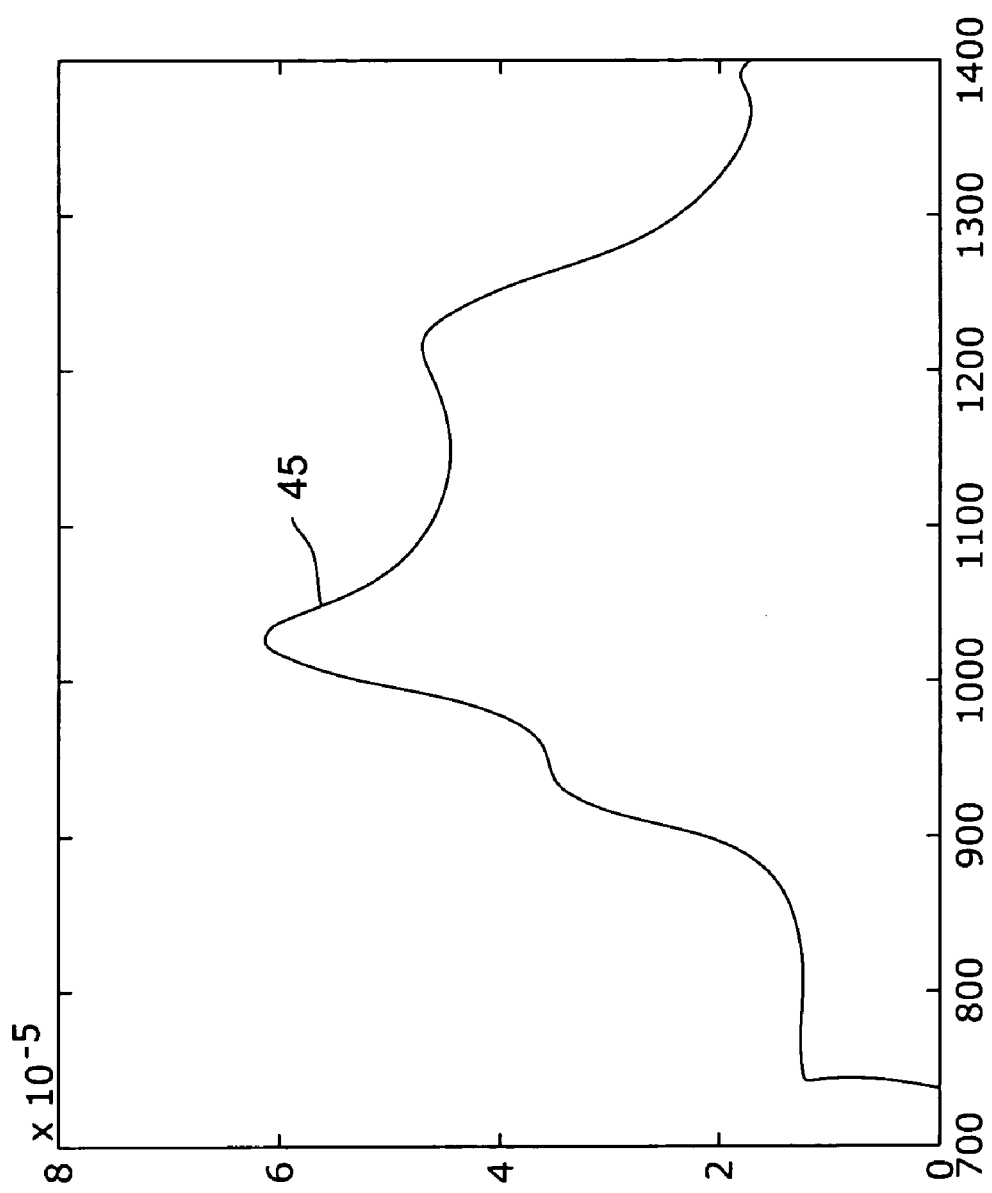
Figure 10C:
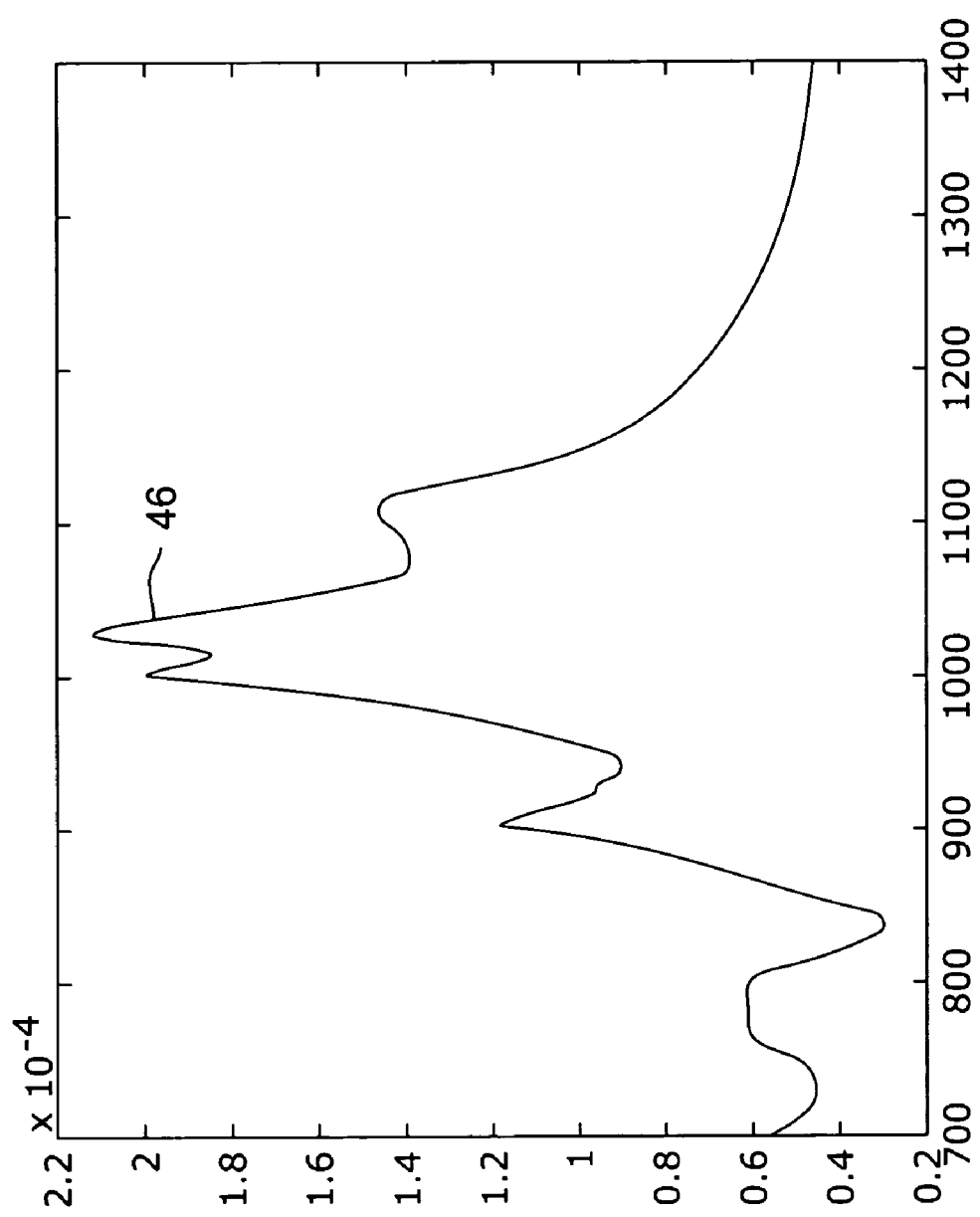
Figure 11:
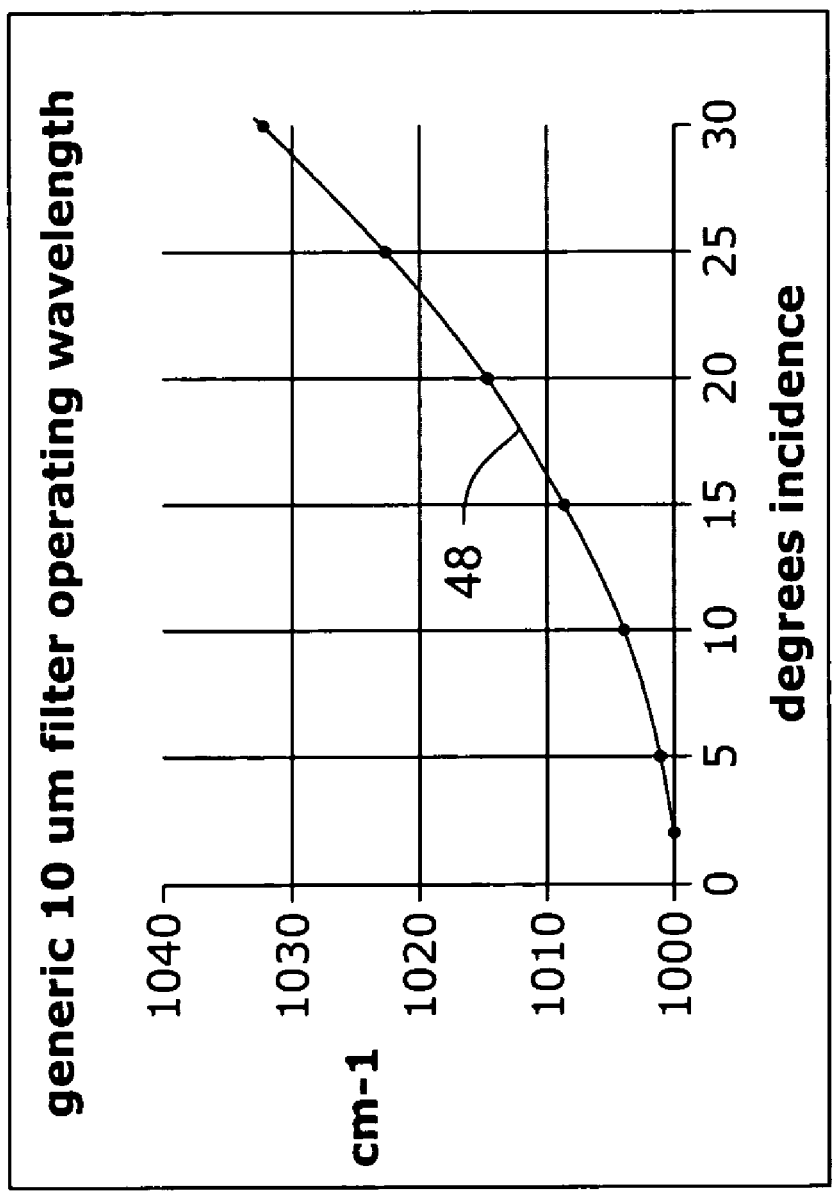
FIG. 11 shows the effect of variation of an angle of incidence on a narrow-band filter.
Figure 12:
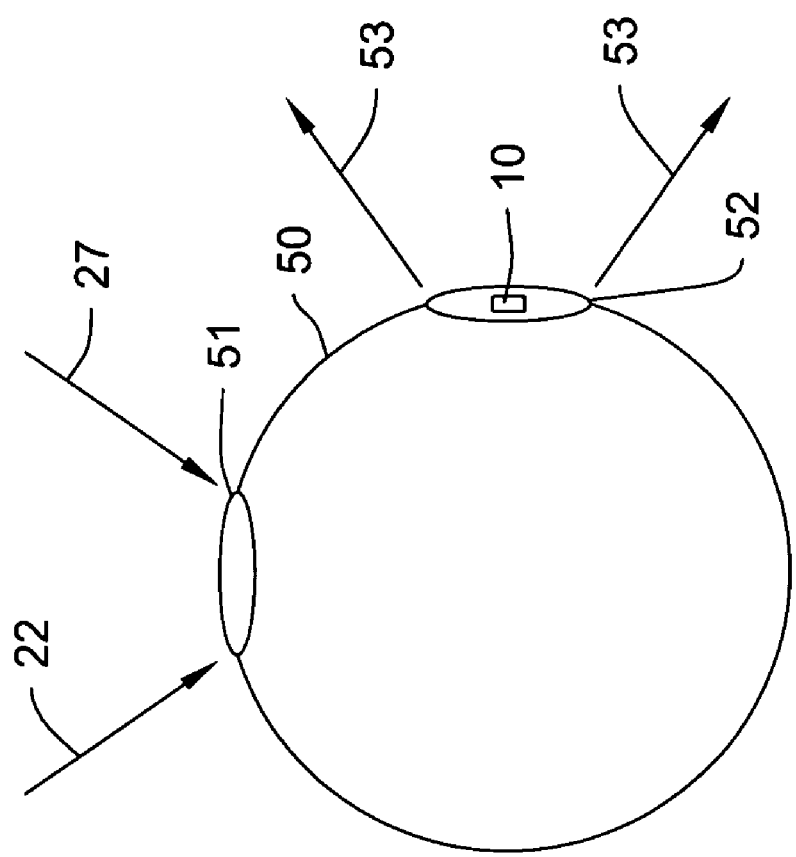
FIG. 12 reveals a light integrating sphere.

Sensor 10 electronics may include a CMOS electronic circuit 40 as shown in FIG. 9 may be used to compute the IR ratio signal of a background signal and a gas detection signal from corresponding detectors 17 to inputs 37 and 38, respectively. IR detector signals pass through preamplifiers 41 and 42 and are digitized with a microprocessor 39 operating in a sigma-delta feedback loop. The ratio signal may be accessed at output 43. An RF link may be connected to output 43. Circuit 40 uses 150 uA at 3V (0.5 mW).

Discrimination between chemical agents and interferents may be detected. The military M21 remote sensing chemical agent alarm and joint service lightweight standoff chemical agent detector (JSLSCAD), which are remote chemical agent sensors, measure the radiance at multiple narrow wavebands within the range 800 to 1200 wavenumbers, where atmospheric transmission is normally good (except for the ozone doublet near 1030 cm-1) and chemical agents have distinctive spectral characteristics. Curves 44, 45 and 46 in FIGS. 10*a*, 10*b* and 10*c* show the absorptivity coefficients of chemical nerve agent GB, and two common battlefield interferents, white phosphorus (WP) smoke and Fort Benning dust (dust) near 10 um wavelength, respectively.

In order to differentiate chemical agents from each other, and from interferents, at least two, and possibly many, different IR wavebands must be measured. For example, looking at FIGS. 10*a*, 10*b* and 10*c*, the relative fractional radiance change at 8.0 um (1250 $cm^{-1}$) compared to 9.8 um (1020 $cm^{-1}$) appears small for GB, but significant for either WP or dust. The spectral resolution that has been used (with M21 and JSLSCAD) to detect and differentiate chemical agents against complex background IR signatures may be 4 wavenumbers. This however may require 100 IR measurement bands to cover the full 8–12 um spectral range, which seems not conducive to a low-cost sensor. Fortunately, the skyward viewing geometry of the proposed sensor greatly simplifies the background IR signature, so that a fewer number of wider spectral bands may be used. Since the minimum practical number, and width, of the wavebands for reliable species identification may need to be determined, one could analytically determine how a variation in the number of IR bands and bandwidths affect the ability of the proposed sensor to discriminate chemical agents from harmless atmospheric contaminants (dust, smoke, etc.) and discriminate different classes and types of chemical agents from each other. One may use IR spectra. One may take into account recent improvements in signal processing and pattern recognition techniques (autoregressive (AR) modeling, Markov Random Field (MRF) and neutral net processing. One may select the smallest number of IR bands, with the widest wavebands, that may produce a useful practical result in sensor 10. The results may be used to determine the optimum number of IR bands and bandwidths required in a production sensor.

A look at this has been performed, using JSLSCAD data as a baseline. This is tended to indicate that higher-resolution is more important than the number of bands employed. Adequate performance may be attained with five to eight wavebands, with full width half maximum (FWHM) of 16 cm-1 (approx 0.2 um). Suitable center-wavebands for various agents are indicated as follows: GA, 1046 cm-1; GB, 1026 cm-1; GD, 1022 cm-1; GF, 1016 cm-1; VX, 1038 cm-1; HD, 1231 cm-1; HN3, 1121 cm-1; and Lewisite, 814 cm-1.

An 8–12 um sensor 10 may be fabricated using circuit 40 of FIG. 9. Sensor 10 may use one 45 degree field of view (FOV) 30×30 mosaic IVP TE IR sensor on one channel, with the other channel being used to measure air temperature with a thermistor. This may be a dual-band IVP TE sensor 10 calibrated radiometer. The 30×30 mosaic TE IVP sensor 10 may be placed in a circular aluminum optical shroud on a circuit board. Two chips, amplifiers 15 (41, 42) and microprocessor 16 (39), and array 14 may be placed on circuit board 47.

For the lowest cost and weight, sensor 10 may use no lens and rely on the overhead chemical agent filling the vertical field of view (FOV). If no lens is used, then incident rays from the sky within the FOV may pass through the narrow-band IR filters at varying angles of incidence. In this case, one may consider the change in IR filter characteristics with angle of incidence. The computed change in center wavelength of a 10 μm bandpass filter as a function of angle of incidence of the radiation shows that plus/minus 25 degrees (i.e., about F/1) may be acceptable, so no collimating lens should be required for 20 cm-1 wavebands and F/1 FOV. A germanium window may be used to provide environmental protection. The window may be made optically diffusing, to provide more uniform fields of view to IR detectors 17. Curve 48 of FIG. 11 shows the effect of variation of an angle of incidence on a generic narrow-band filter centered at 1000 cm-1 (10 um wavelength).

It is significant that the fields of view of the groups of detectors 17 for the different IR bands be essentially identical, so that point objects (dust specs, isolated clouds, etc.) do not affect one band more than another. This may be substantially achieved by the use of a mosaic of IR detector 17 and IR filters 34, with every detector operating in one band being surrounded by other sensors operating in the different bands, as described above. Impinging radiation 27 field can also be substantially randomized by the use of an "integrating sphere" 50 as shown in FIG. 12. Radiation 27 may enter a portal 51 of sphere 50. Radiation 27 is reflected around internally in sphere 50 by the reflective inside surface of sphere 50. Randomized radiation 53 may exit from sphere 50 through portal 52. However, sensor 10 may be placed at the portal 52 exit of sphere 50 to detect the radiation.

Sensor 10 has high shock tolerance. IR detectors 17 have been tested to 14,000 g, and may tolerate more than 20,000 g. Electronic circuits may be hardened to 20,000 g by encapsulation in supporting media. Lens components might be able to tolerate 20,000 g with suitable robust mounts.

Weight, size and power of sensor 10 may be favorable for many users. Using the known density of materials, one may estimate the weight of the expected components of chemical agent sensor 10. A single band sensor 10 is reviewed in the weight calculation table 54 in FIG. 13. Additional infrared bands may be added with little additional impact in size/weight/power/cost.

The present detector system 60 may receive emissions 56 from a gas cloud or sample 55. System 60 may be mounted so as to receive emissions or radiation 56 from the sky or the ground. The spectrum of the cloud or sample may be better detected if the cloud or sample 55 is at a temperature different from the sky or the ground. System 60 may be a stand off detector in that it detects gas at a distance. Another kind of sensor may be a point sensor in that it is in the gas being detected, i.e., it may be pointed into the gas. Emissions or incident radiation 56, for instance, may propagate through a collimating lens 57 to beam splitter 58. Lens 57 may be composed of an infrared transparent material such as Ge. Splitter 58 may have about a 50/50 ratio split between transmittance and reflection. A thin layer of infrared reflective material such as aluminum may be deposited on or applied to a flat surface on the front of the infrared transparent material of splitter 58 facing the incident radiation 56. Incident radiation or beam 56 may be split into beams 61 and 62 by splitter 58. Beam 61 may go from splitter 58 to be reflected by fixed mirrors 63 and 64 in that order, and then at least partially pass through splitter 58 to a cylindrical focusing lens 65. Beam 62 may emanate from splitter 58 towards mirror 64 and be reflected towards mirror 63 which in turn may reflect beam 62 to splitter 58. Splitter 58 may reflect at least a portion of beam 62 to lens 65. Beams 61 and 62 may meet at an area 66 on the top flat surface of lens 65 to interfere with each other to form a fringe or interference pattern 81 having fringes or lines 82.

Lens 65 may magnify or focus in one dimension, in that it may have one dimension of curvature. The lens 65 material may be composed of some infrared transparent substance such as Ge. Ordinary glass does not appear to adequately transmit such IR light.

The lens 57, splitter 58, and fixed mirrors 63 and 64 may constitute a stationary linear fringe interferometer. Use of a stationary interferometer may result in better sensitivity and resolution than an interferometer with a moveable mirror 63 or 64. Minor movement of an unfixed mirror may adversely affect the performance of the interferometer, even if the moveable mirror is supposedly adjusted for optimal performance.

Figure 14:
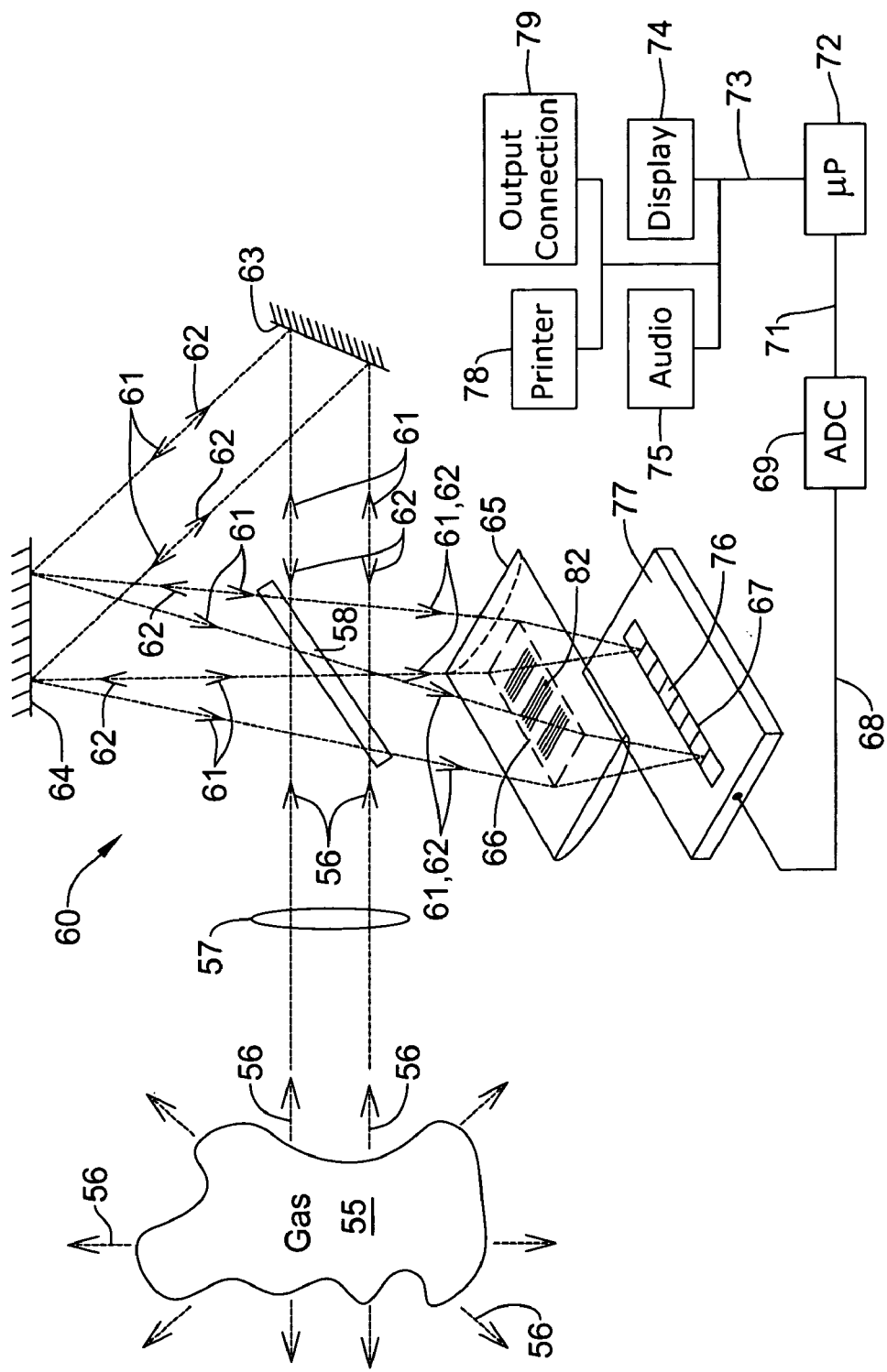
FIG. 14 is a diagram of a multi-band gas sensor.

Light beams 61 and 62 may impinge about an area 66. If light beams 61 and 62 interfere, there may be the fringe pattern 81 having fringes or interference lines 82, as shown in area 66 on the top flat surface of cylindrical lens 65 in FIG. 14 and of pattern 81 in FIG. 15. Pattern 81 in the graph is an illustrative example of a number, shape and intensity of fringes which may be different for various systems. The graph shows the intensity of the light impinging the top surface of lens 65 versus distance in the direction of the length of longitudinal axis of lens 65. The lines or fringes 82 of interference pattern 81 may be focused by lens 65 onto detectors 76 situated in a linear array 67. The lines or fringes may be individually focused on respective detectors 76. Each detector 75 may sense the light and its intensity at each increment of distance of the pattern 81, and convert its respective intensity locations into electrical signal representing the intensity of the light at each of the detectors 76 in array 67, of which the electrical signals together may provide an electrical representation of interference pattern 81. Linear array 67 may be a row of about 120 uncooled infrared detectors such as microbolometers, in a case of an illustrative example. The number of detectors may be more or less than 120. The microbolometers may be reasonable in cost and do not need to be cooled.

The output signals from the array 67 may be low level voltages and easy to manage with the present electronics. The uncooled infrared detectors 76 may provide broadband detection from about one to fifty microns. A typical range of infrared detection may be between about 3 and 12 microns. On the other hand, there may be visible and ultra-violet light detectors 76 in the array for other band detection. The whole system 60 may be designed to detect most fluids (i.e., gases or liquids) or be designed for optimized detection of a particular fluid.

Figure 15:
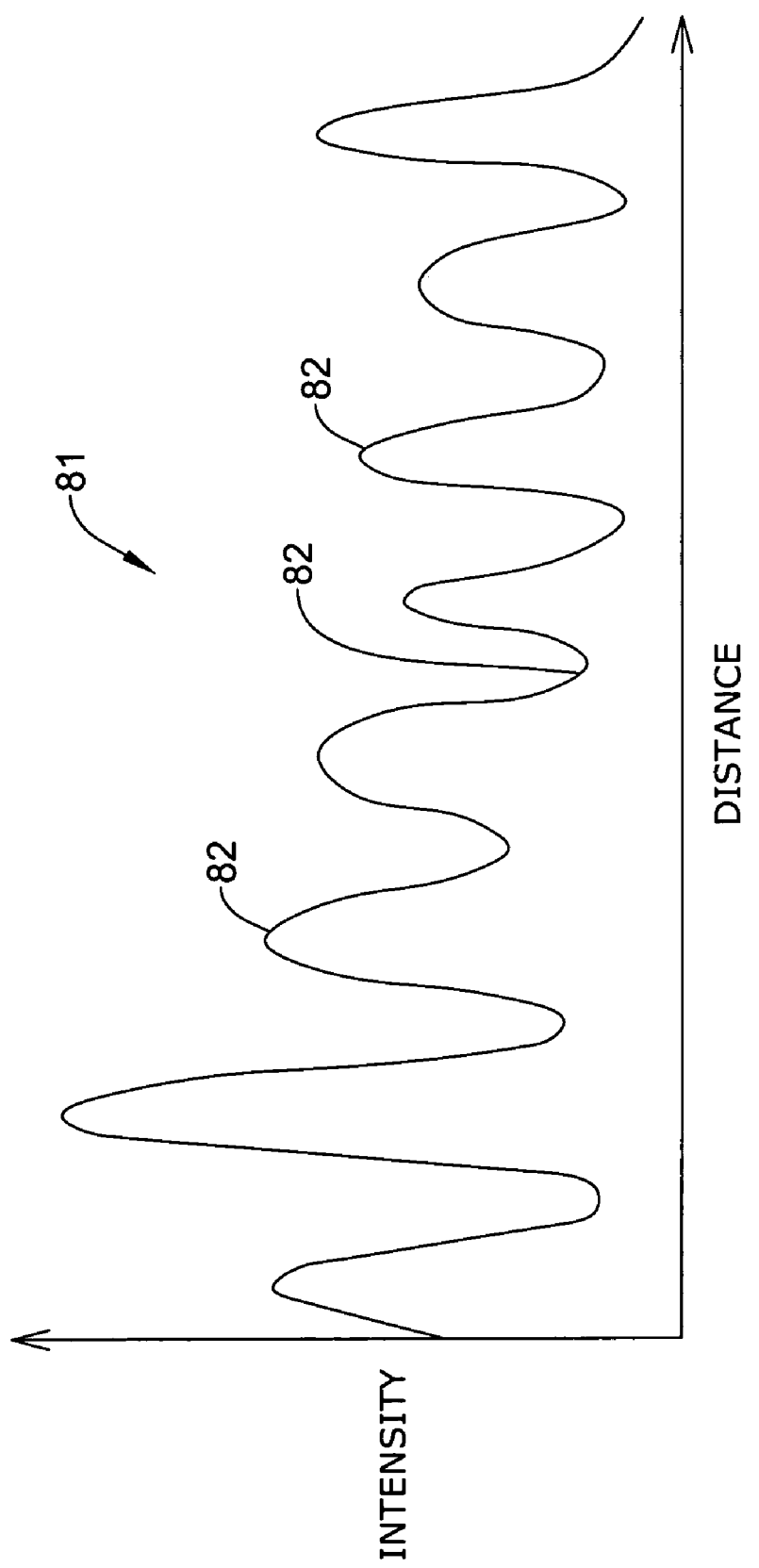
FIG. 15 is a graph of an interference pattern of light that impinges a linear detector array.

Items 82 of the plot in FIG. 15 may represent the interference pattern 81 of the impinging light. There may be more or less fringes or lines 82, each of which may be focused on a detector 76 in the linear array 67. The electrical signals 68, which may be electrical equivalents of the lines or fringes 82 impinging the detectors 76, may be conveyed from array 67 via a conductive line to an analog-to-digital converter (ADC) 69. The signals 68 may be converted into digital signals 71 representative of intensities of the light impinging each of the detectors 76 in array 67. The detectors 76 may be situated in an integrated vacuum package (IVP) 77 with a window over the detectors to maintain the integrity of the package. The signals 71 may be sent to a microprocessor 72 in either a serial or parallel format. These signals 71 may be processed or deconvolved into data that provides a pattern of a "fingerprint" or other identifying pattern of the sample gas or gases 55. The conversion of signals 71 to signals 73 constituting an identifying pattern may be performed by processor 72 utilizing an available Fourier transform program. FIG. 16 shows a graphical representation of such pattern 83 having features 84 in terms of intensity versus wavelength. Processor 72 may have an analyzer with a look-up table to recognize a pattern 83 or the electronic signals 68 from the array 67. Pattern 83 may be displayed on display 74. The output 73 of processor 72 may include identification of the detected gas or gases by name or otherwise, and provide an overall relative intensity and average wavelength or frequency of the gas radiation, in addition to the spectrum such as the intensity versus wavelength or power versus frequency data, for example. The spectrum may be expressed in various sets of terms. Other information may be provided by processor 72. The output 73 of processor 72 may go to a display 74, so that the observer may observe the data, graphs, and processor analyses. Each analysis in an illustrative example may cover about 100 different wavelengths. The number of wavelengths may instead be more or less that 100. An output 73 to an audio emanating device 75 and display 74 may be provided to the user in terms of intensities, wavelengths, and identities of the gases, or other kinds of parameters or data. Also, the display 74 and device 75 may provide visible and audio warnings about the presence of certain gases and their intensities, particularly if they are considered dangerous in particular areas. There may be warning lights and alarms. The output 73 may also go to a printer 78 and an external connection 79.

The sensor may be constructed with available and inexpensive parts to result in reasonable, practical, reasonable and saleable product. The system 60 may be put into a package, for example, of about a 10 cm cube, excluding the printer 78. This package may also exclude warning lights, alarms and sirens. It may or might not include the display and audio device. System 60 and its package may have the flexibility of being designed to fit the needs or desires of the user.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A chemical agent sensor comprising:
   an interferometer having a light input and output;
   an array of light detectors proximate to the output of the interferometer; and
   a processor connected to the array; and
   wherein:
   the array is a linear array; and
   the interferometer is a linear fringe interferometer.

2. The sensor of claim 1, wherein the lens is a cylindrical lens having a longitudinal axis approximately parallel to the longitudinal dimension of the linear array.

3. The sensor of claim 2, wherein the light detectors are infrared light detectors.

4. The sensor of claim 3, wherein the linear array of light detectors are arranged so that some detectors are positioned to detect a different range wavelengths than another detector in the array.

5. The sensor of claim 4, wherein the detectors are uncooled intensity detectors of light.

6. The sensor of claim 5, wherein the processor has an intensity versus wavelength display.

7. The sensor of claim 6, wherein light from a gas enters the light input of the interferometer.

8. The sensor of claim 7, wherein the processor comprises a Fourier transform mechanism.

9. The sensor of claim 8, wherein the processor comprises a gas identification indicator.

10. The sensor of claim 9, wherein the indicator is a display.

11. The sensor of claim 9, wherein the indicator is an audio device.

12. The sensor of claim 9, wherein the indicator is a printer.

13. A means for sensing gas, comprising:
    means for receiving light emanated by the gas;
    means for interfering the light into a linear fringe pattern;
    means for detecting the linear fringe pattern of light and converting the pattern into electrical signals; and
    means for processing the electrical signals into an intensity versus wavelength parameters of the gas; and
    wherein the means for detecting is uncooled infrared detection.

14. A method for sensing gas, comprising:
    receiving light emanated by the gas;
    interfering the light into a pattern of intensity versus distance;
    detecting the pattern and converting the pattern into electrical signals; and
    processing the electrical signals into a pattern of intensity versus distance; and
    wherein the detecting is performed with uncooled infrared detectors.

15. The method of claim 14, wherein the processing comprises a Fourier transform mechanism.

16. An apparatus for sensing a fluid, comprising:
    an interferometer having an input proximate to the fluid and having an output;
    a linear array of infrared light detectors proximate to the output;
    a processor connected to detectors; and
    an intensity versus wavelength output device connected to the processor; and
    wherein light from the fluid into the input of the interferometer is output from the interferometer in a distance versus wavelength fringe pattern.

17. The apparatus of claim 16, wherein
    the output device provides intensity versus wavelength data about the fluid; and
    the output device identifies the fluid proximate to the input.

18. The apparatus of claim 16, wherein light from the fluid into the input of the interferometer is output from the interferometer in a distance versus wavelength linear fringe pattern.

19. The apparatus of claim 18, wherein the interferometer comprises
    a first lens at the input;
    an infrared light splitter proximate to the lens and the output;
    a first mirror proximate to the splitter; and
    a second mirror proximate to the splitter and the first mirror.

20. The apparatus of claim 19, wherein the first and second mirrors are fixed relative to each other.

21. The apparatus of claim 20, wherein the fringe pattern is converted by the array of detectors into electrical signals.

22. The apparatus of claim 21, wherein the processor converts the electrical signals to spectrum data of the fluid.

23. The apparatus of claim 22, wherein the processor identifies the fluid.

24. The apparatus of claim 23, wherein the processor utilizes a Fourier transformation to convert the electrical signals to spectrum data of the fluid.

25. The apparatus of claim 24, wherein
    the detectors are uncooled.

26. The apparatus of claim 25, further comprising second lens that is a longitudinal focusing lens situated between the output of the interferometer and the array.

27. The apparatus of claim 26, wherein:
    the first lens is a collimating lens;
    the first lens is transparent to infrared light;
    the second lens is transparent to infrared light; and
    the splitter is reflective of infrared light and transparent to infrared light.

28. The apparatus of claim 27, wherein the spectrum data are intensity versus wavelength.

29. The apparatus of claim 27, wherein the spectrum data are power versus frequency.

* * * * *